(12) United States Patent
Perschbacher et al.

(10) Patent No.: US 11,298,068 B2
(45) Date of Patent: Apr. 12, 2022

(54) SYSTEMS AND METHODS FOR DETECTING ARRHYTHMIAS

(71) Applicant: Cardiac Pacemakers, Inc., St. Paul, MN (US)

(72) Inventors: David L. Perschbacher, Coon Rapids, MN (US); Deepa Mahajan, North Oaks, MN (US); Sunipa Saha, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 143 days.

(21) Appl. No.: 16/705,732

(22) Filed: Dec. 6, 2019

(65) Prior Publication Data

US 2020/0178829 A1  Jun. 11, 2020

Related U.S. Application Data

(60) Provisional application No. 62/776,291, filed on Dec. 6, 2018.

(51) Int. Cl.
*A61B 5/00* (2006.01)
*A61B 5/363* (2021.01)
*A61B 5/316* (2021.01)

(52) U.S. Cl.
CPC ............. *A61B 5/363* (2021.01); *A61B 5/316* (2021.01); *A61B 5/4836* (2013.01)

(58) Field of Classification Search
CPC .............................................. A61B 5/349–366
See application file for complete search history.

(56) References Cited

U.S. PATENT DOCUMENTS

2002/0065473 A1* 5/2002 Wang ................. A61B 5/02405
600/518
2016/0045125 A1 2/2016 Krueger et al.
(Continued)

FOREIGN PATENT DOCUMENTS

WO    WO-9302746 A1    2/1993
WO    WO-2016118841 A1    7/2016
WO    WO-2020118154 A1    6/2020

OTHER PUBLICATIONS

"International Application Serial No. PCT/US2019/064879, International Preliminary Report on Patentability dated Jun. 17, 2021", 10 pgs.

(Continued)

*Primary Examiner* — Scott M. Getzow
(74) *Attorney, Agent, or Firm* — Schwegman Lundberg & Woessner, P.A.

(57) ABSTRACT

Systems and methods for detecting cardiac arrhythmias such as atrial tachyarrhythmia (AT) are discussed. An exemplary system includes a ventricular beat analyzer circuit to detect ventricular beats and assess ventricular activity, such as to evaluate a ventricular rate stability. The system includes an arrhythmia detector circuit to detect respective AT indications in distinct time periods using portions of received physiologic information during the distinct time periods. A control circuit can monitor the ventricular beats on a beat-by-beat basis, in response to the detected ventricular beats satisfying an instability condition, trigger AT detections during the distinct time periods and withhold AT detection in a subsequent time period if no AT is detected in the present time period. An AT characteristic may be generated using the detected AT indications. A therapy may be delivered in accordance with the AT characteristic.

20 Claims, 6 Drawing Sheets

(56) References Cited

U.S. PATENT DOCUMENTS

2018/0104502 A1    4/2018  Perschbacher et al.
2018/0192902 A1    7/2018  Perschbacher et al.
2018/0256059 A1    9/2018  Perschbacher et al.

OTHER PUBLICATIONS

"International Application Serial No. PCT/US2019/064879, International Search Report dated Feb. 28, 2020", 4 pgs.
"International Application Serial No. PCT/US2019/064879, Written Opinion dated Feb. 28, 2020", 8 pgs.

* cited by examiner

SYSTEMS AND METHODS FOR DETECTING ARRHYTHMIAS

CLAIM OF PRIORITY

This application claims the benefit of priority under 35 U.S.C. § 119(e) of U.S. Provisional Patent Application Ser. No. 62/776,291, filed on Dec. 6, 2018, which is herein incorporated by reference in its entirety.

TECHNICAL FIELD

This document relates generally to medical devices, and more particularly, to systems, devices and methods for detecting and managing cardiac arrhythmias.

BACKGROUND

Implantable medical devices (IMDs) have been used for monitoring patient health condition or disease states and delivering therapies. For example, implantable cardioverter-defibrillators (ICDs) may be used to monitor for certain abnormal heart rhythms and to deliver electrical energy to the heart to correct the abnormal rhythms. Some IMDs may be used to monitor for chronic worsening of cardiac hemodynamic performance, such as due to congestive heart failure (CHF), and to provide cardiac stimulation therapies, including cardiac resynchronization therapy (CRT) to correct cardiac dyssynchrony within a ventricle or between ventricles.

Some IMDs can detect cardiac arrhythmias, such as atrial tachyarrhythmia (AT). One type of AT event is atrial fibrillation (AF), recognized as the most common clinical arrhythmia affecting millions of people. During AF, disorganized electrical pulses originated from regions in or near an atrium may lead to irregular conductions to ventricles, thereby causing inappropriately fast and irregular heart rate. AF may be paroxysmal that may last from minutes to days before it stops by itself. Persistent AF may last for over a week and typically requires medication or other treatment to revert to normal sinus rhythm. AF is permanent if a normal heart rhythm cannot be restored with treatment. AF may be associated with stroke and requires anticoagulation therapy.

Another type of AT event is atrial flutter (AFL). AFL usually accompanies with some degree of atrioventricular (AV) node conduction block, and can be associated with a fast and usually regular heart rate. Typical or Type I AFL may involve a single reentrant circuit in the right atrium around the tricuspid valve annulus, and has an atrial rate of 240 to 340 beats per minute (bpm). The reentrant circuit most often travels in a counter-clockwise direction. Atypical or Type II AFL follows a different circuit, which may involve the right or the left atrium, and usually has a faster atrial rate of around 340-440 bpm. AFL may be associated with a variety of cardiac disorders, such as coronary artery disease (CAD) or hypertensive heart disease. AFL may often degenerate into AF. Prolonged fast AFL may lead to decompensation with loss of normal heart function. This may manifest as effort intolerance, nocturnal breathlessness, or swelling of the legs or abdomen.

Timely detection of atrial tachyarrhythmia, such as AF or AFL, may be clinically important for assessing cardiac function. Some atrial tachyarrhythmia may be characterized by slow and stable ventricular rates. Such atrial tachyarrhythmia episodes may be mistakenly recognized by an IMD as a sinus rhythm, and are undetected or under-detected in some patients. This may have an adverse impact on patient outcome.

OVERVIEW

Embodiments of systems, devices, and methods discussed in this document can improve device-based cardiac arrhythmia detection and patient management. An exemplary system includes a ventricular beat analyzer circuit that can detect ventricular beats and assess ventricular activity, such as evaluating ventricular rate stability. The system includes an arrhythmia detector circuit to detect respective AT indications in distinct time periods using portions of received physiologic information during the distinct time periods. A control circuit can trigger detection of AT indications in response to the detected ventricular beats satisfying a specific condition, and withhold AT detection in a subsequent time period if no AT is detected in the present time period. An AT characteristic may be generated using the detected AT indications. The system may initiate or adjust a therapy using the generated AT characteristic.

Example 1 is a system for detecting atrial tachyarrhythmia (AT). The system comprises a ventricular beat analyzer circuit, an arrhythmia detector circuit, and a control circuit. The ventricular beat analyzer circuit is configured to receive physiologic information of a patient and to detect ventricular beats using the received physiologic information. The arrhythmia detector circuit is configured to detect respective AT indications in distinct time periods using portions of the received physiologic information during the distinct time periods. The control circuit is configured to monitor the ventricular beats on a beat-by-beat basis, and in response to the ventricular beats satisfying an instability criterion indicative of unstable ventricular rate, trigger the arrhythmia detector circuit to detect the respective AT indications in distinct time periods using stability of ventricular beats in the distinct time periods. The control circuit can determine an AT characteristic using the detected respective AT indications.

In Example 2, the subject matter of Example 1 optionally includes the ventricular beat analyzer circuit that can be configured to evaluate a ventricular rate stability (VRS) using the detected ventricular beats, and the control circuit that can be configured to trigger the arrhythmia detector circuit to detect the respective AT indications in distinct time periods in response to the VRS satisfying the instability criterion, and in response to an AT indication indicating an absence of AT in one of the distinct time periods, control the arrhythmia detector circuit to withhold detection of AT indication in a time period subsequent to the one of the distinct time periods, and trigger the ventricular beat analyzer to assess ventricular activity. The distinct time periods can include a time period preceding in time a determination of the VRS satisfying the instability criterion.

In Example 3, the subject matter of Example 2 optionally includes the control circuit that can be configured to: trigger the arrhythmia detector circuit to detect a first AT indication during a first time period in response to the VRS satisfying the instability criterion; if the first AT indication indicates a presence of AT in the first time period, control the arrhythmia detector circuit to detect a second AT indication during a subsequent second time period; and if the first AT indication indicates an absence of AT in the first time period, control the arrhythmia detector circuit to withhold detection of the second AT indication during the subsequent second time period, and trigger the ventricular beat analyzer circuit to evaluate the VRS.

In Example 4, the subject matter of Example 3 optionally includes the distinct time periods that are consecutive in time.

In Example 5, the subject matter of any one or more of Examples 3-4 optionally includes the control circuit that can be further configured to: if the second AT indication indicates a presence of AT in the second time period, control the arrhythmia detector circuit to detect a third AT indication during a third time period subsequent to the second time period; if the second AT indication indicates an absence of AT in the second time period, control the arrhythmia detector circuit to withhold detection of the third AT indication, and trigger the ventricular beat analyzer circuit to evaluate the VRS; and determine the AT characteristic using one or more the first, second, or third AT indication.

In Example 6, the subject matter of any one or more of Examples 3-5 optionally includes the control circuit that can be configured to determine the first time period that precedes a time of determining the VRS satisfying the instability criterion.

In Example 7, the subject matter of any one or more of Examples 3-6 optionally includes the arrhythmia detector circuit that can be configured to detect the AT characteristic including detecting an onset of an AT episode using the received physiologic information during the first time period.

In Example 8, the subject matter of Example 7 optionally includes, if the second AT indication indicates an absence of AT in the second time period, the arrhythmia detector circuit can be configured to detect the AT characteristic including detecting a termination of the AT episode using the received physiologic information during the second time period.

In Example 9, the subject matter of Example 8 optionally includes the arrhythmia detector circuit that can be configured to detect the AT characteristic including a duration of the AT episode from the detected onset to the detected offset of the AT episode.

In Example 10, the subject matter of any one or more of Examples 2-9 optionally includes the ventricular beat analyzer circuit that can be configured to evaluate the VRS using a count of unstable cardiac cycles within a specific time period or a specific number of cardiac cycles, the unstable cardiac cycle corresponding to a cycle length difference from a preceding cycle length exceeding a threshold; and the control circuit that can be configured to determine that the VRS indicates an unstable ventricular rate if the count of unstable cardiac cycles exceeds a count threshold.

In Example 11, the subject matter of any one or more of Examples 2-9 optionally includes the ventricular beat analyzer circuit that can be configured to initialize the VRS using a variability measure of cycle lengths of a plurality of cardiac cycles, and to adaptively update the VRS using a cycle length difference between a present cycle length and a preceding cycle length; and the control circuit that can be configured to determine that the VRS indicates an unstable ventricular rate if the adaptively updated VRS exceeds a threshold value.

In Example 12, the subject matter of any one or more of Examples 2-11 optionally includes the ventricular beat analyzer circuit that can be configured to determine the instability criterion using a patient medical condition.

In Example 13, the subject matter of any one or more of Examples 1-12 optionally includes the arrhythmia detector circuit that can be configured to detect the respective AT indications in the distinct time periods using one or more of ventricular rate variability or ventricular signal morphology within the distinct time periods.

In Example 14, the subject matter of Example 13 optionally includes the arrhythmia detector circuit that can be configured to: determine a count of unstable cardiac cycles within the specific time period, the unstable cardiac cycle corresponding to a cycle length difference ($\Delta$CL) from a preceding cycle length exceeding a threshold; and detect the AT indication indicating a presence of AT in the specific time period if the count of unstable cardiac cycles exceeds a threshold count.

In Example 15, the subject matter of any one or more of Examples 1-14 optionally includes the ventricular beat analyzer circuit that can be configured to generate a physiologic feature including one or more of a ventricular rate, a ventricular activation pattern, a ventricular signal morphology, or a cardiac event between consecutive ventricular beats; and the control circuit is configured to trigger the arrhythmia detector circuit to detect the respective AT indications in response to the generated physiologic feature satisfying a condition.

Example 16 is a method for detecting atrial tachyarrhythmia (AT). The method comprises steps of: receiving physiologic information of a patient; detecting ventricular beats and assessing ventricular activity using the received physiologic information via a ventricular beat analyzer circuit; monitoring the ventricular beats on a beat-by-beat basis, and in response to the detected ventricular beats satisfying a specific condition, triggering detection of respective AT indications in distinct time periods using stability of ventricular beats in the distinct time periods via an arrhythmia detector circuit; in response to an AT indication indicating an absence of AT in one of the distinct time periods, withholding detection of AT indication in a time period subsequent to the one of the distinct time periods, and re-assessing ventricular activity via the ventricular beat analyzer; and generating an AT characteristic using the detected respective AT indications.

In Example 17, the subject matter of Example 16 optionally includes steps of assessing the ventricular activity incudes evaluating a ventricular rate stability (VRS) using the detected ventricular beats and triggering detection of respective AT indications in distinct time periods is in response to the VRS satisfying an instability criterion indicative of unstable ventricular rate.

In Example 18, the subject matter of Example 17 optionally includes steps of triggering detection of a first AT indication during a first time period in response to the VRS satisfying the instability criterion, detecting a second AT indication during a subsequent second time period if the first AT indication indicates a presence of AT in the first time period, and withholding detection of the second AT indication during the subsequent second time period, and re-assessing ventricular activity if the first AT indication indicates an absence of AT in the first time period.

In Example 19, the subject matter of Example 18 optionally includes steps of: generating the AT characteristic includes one or more of: detecting an onset of an AT episode using the received physiologic information during the first time period; detecting a termination of the AT episode using the received physiologic information during the second time period if the second AT indication indicates an absence of AT in the second time period; or determining an AT episode duration from the detected onset to the detected offset of the AT episode.

In Example 20, the subject matter of any one or more of Examples 17-19 optionally includes steps of: evaluating the VRS includes determining a count of unstable cardiac cycles within a specific time period or a specific number of cardiac cycles, the unstable cardiac cycle corresponding to a cycle length difference (ΔCL) from a preceding cycle length exceeding a threshold; and determining that the VRS satisfies an instability criterion if the count of unstable cardiac cycles exceeds a count threshold.

In Example 21, the subject matter of any one or more of Examples 17-20 optionally includes steps of: evaluating the VRS includes initializing the VRS using a variability measure of cycle lengths of a plurality of cardiac cycles, and adaptively updating the VRS using a cycle length difference (ΔCL) between a present cycle length and a preceding cycle length; and determining that the VRS satisfies an instability criterion if the adaptively updated VRS exceeds a threshold value.

In Example 22, the subject matter of any one or more of Examples 16-21 optionally includes the distinct time periods are consecutive time periods, and triggering detection of respective AT indications involves using one or more of ventricular rate variability or ventricular signal morphology within the distinct time periods.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
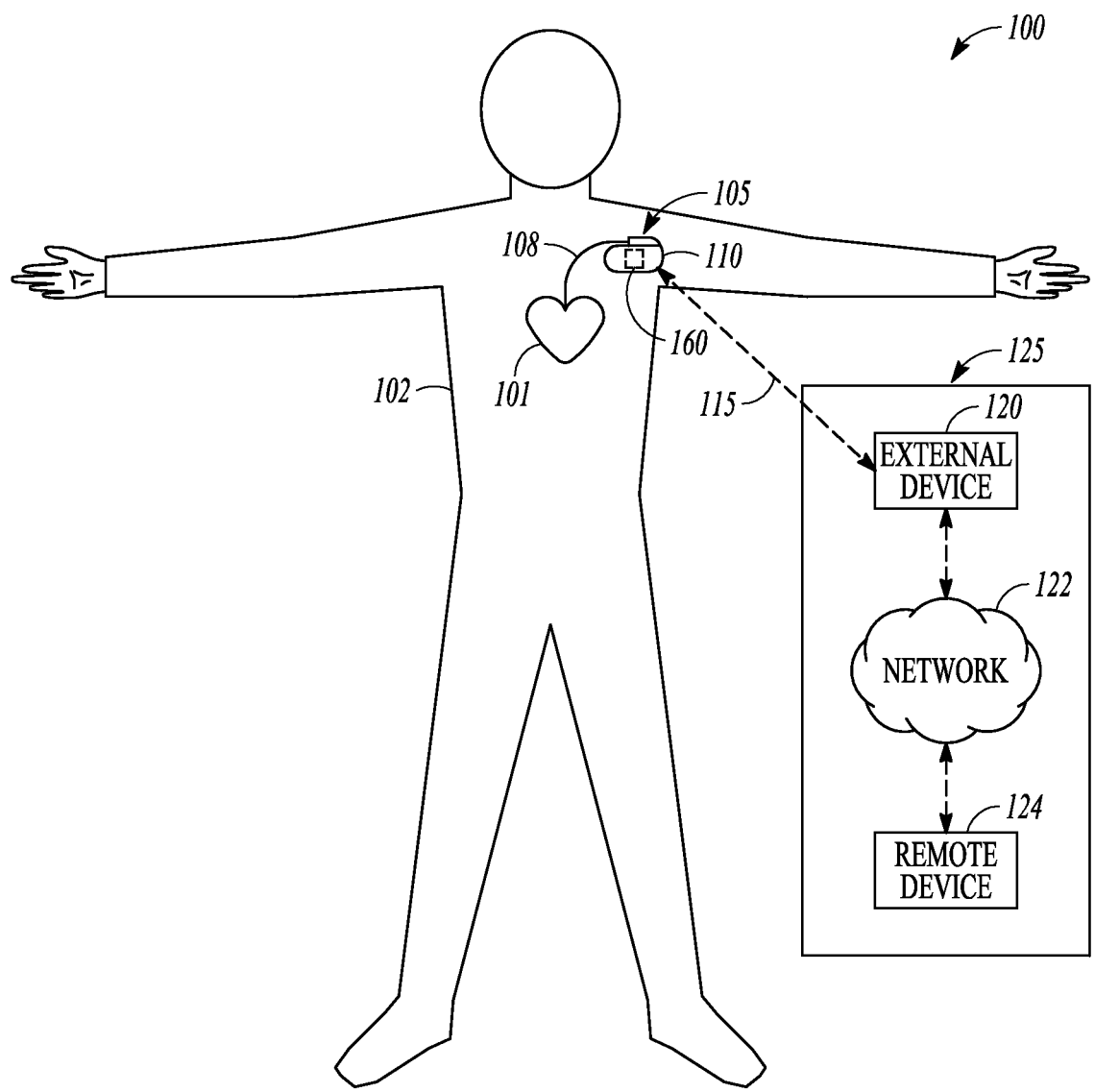
FIG. 1 illustrates generally an example of a patient management system and portions of an environment in which the system may operate.

Atrial tachyarrhythmia, such as AF or AFL, are characterized by fast atrial rate, and in some patients, increased variability of ventricular heart rate. In some patients, direct sensing of atrial activation rate with an electrode positioned in or near the atrium is not available or not feasible, such as patients not indicated for atrial lead implantation. A medical device, such as a single-chamber IMD with no dedicated atrial sensing/pacing lead, may detect AT based on ventricular heart rate, without direct sensing of atrial activity. However, confounding factors such as noise, motion artifacts, or cardiac rhythms other than the AT may be mistakenly detected as AT events. For example, during AFL, impulses from the atria are conducted to the ventricles through the atrio-ventricular node (AV node). Due primarily to its longer refractory period, the AV node may exert a protective effect on heart rate at the ventricle by blocking atrial impulses in excess of approximately 180 beats per minute (bpm). If an AFL rate is 300 bpm, a two-to-one (2:1) heart block may develop such that only half of the atrial impulses can be conducted to the ventricle, resulting in a ventricular rate of 150 bpm. In some cases, the refractoriness of the AV node may lead to irregular AV conductions, resulting in unstable ventricular rates.

Arrhythmia can be detected using a comparison of a signal metric generated from a physiologic signal to a detection criterion. To reduce computational burden, evaluation of the AT detection criterion may be performed periodically rather than on a beat-by-beat basis. For example, a boxcar function with a non-zero portion having a specified duration may be applied to a cardiac signal to generate a signal segment, and an AT detection criterion may be evaluated within the generated signal segment. The boxcar function can slide in time to generate signal segments in consecutive windows or timer periods, where further evaluations of the AT detection criterion may be performed. As such, the boxcar-based AT detection algorithm can effectually detect AT on a periodic basis.

Periodic assessment of AT detection criterion as in the boxcar-based AT detection algorithm can reduce computational burden. However, in some cases, it may be less sensitive in detecting AT episodes. For example, if an AT episode begins, or terminates, at some point in the middle of a boxcar function, the AT detection criterion may not be satisfied in that boxcar function-defined signal segment. Accordingly, a portion of the underlying tachyarrhythmia (corresponding to the boxcar function-defined signal segment) may be under-detected. Depending on the duration T of the boxcar function, some AT episodes that sustained for a short period of time (e.g., less than T seconds) may be entirely under-detected. Under-detection of a portion, or an entirety, of an AT episode may lead to inaccurate estimation of AT burden and other AT diagnostics.

Moreover, the boxcar-based AT detection algorithm may not provide certain AT diagnostics of clinical interest, such as onset and termination of an AT episode, with adequate precision. For example, the boxcar function generally may not align with the onset and termination of the AT episode. The decision of whether the AT detection criterion is satisfied within a boxcar function-defined signal segment may not adequately indicate a beginning (onset) or an end (termination) of an AT episode. Inaccurate onset and termination timing may lead to false decision regarding AT sustainability, inaccurate estimate of AT burden, etc. As a result, arrhythmia therapy or other clinician intervention may also be inappropriately withheld or delay.

The issues pertaining to boxcar-based AT detection as discussed above may be affected by the choice of boxcar function, such as a duration T of the boxcar function. For example, boxcar functions with a shorter duration (i.e., a shorter window or time period) may help reduce the likelihood of AT under-detection, and lessen the impact of inaccurate detection of AT onset and termination timing on AT burden estimate. However, as the duration of the boxcar duration becomes shorter, it may more likely introduce additional false positive detections, and substantially decrease the AT detection specificity. Such inappropriate detections may decrease detection, result in lack of treatment or untimely treatment, or unnecessary or inappropriate therapies. A shorter boxcar function duration also means that more frequent evaluation of AT detection criterion. Consequently, computational burden and power consumption may be increased. Moreover, false alerts to clinicians of the inappropriately detected arrhythmia, or presenting to clinicians a large volume of inappropriately detected arrhythmic events for review or adjudication, may adversely affect the device efficacy and unwarrantedly increase the healthcare cost associated with patient management. Consequently, this may diminish the clinical utility of the heart rate-based AT detection.

The present inventors have recognized a challenge in AT detection, particularly boxcar-based AT detection as discussed above. Simple solutions such as reducing the duration of boxcar function, may not adequately balance sensitivity or specificity in AT detection (e.g., under-detection or false detection of AT events associated with long duration, and reduced computation efficiency and increased power consumption associated with short duration). Disclosed herein are systems, devices, and methods that can improve cardiac arrhythmias, such as atrial tachyarrhythmia. An exemplary system includes a ventricular beat analyzer circuit that can detect ventricular beats and assess ventricular activity, such as a ventricular rate stability (VRS). An arrhythmia detector circuit can detect respective AT indications in distinct time periods using portions of the received physiologic information during the distinct time periods. A control circuit can trigger the arrhythmia detector circuit to detect the respective AT indications in distinct time periods in response to the detected ventricular beats satisfying a specific condition. In response to an indication of an absence of AT in one of the distinct time periods, the control circuit can withhold detection of AT indication in a time period subsequent to the present time period, and trigger the ventricular beat analyzer circuit to reassess ventricular activity. An AT characteristic may be generated using the detected AT indications. The system can initiate or adjust a therapy in accordance with the AT characteristics.

The systems, devices, and methods discussed in this document may improve the medical technology of automated cardiac rhythm management (CRM) and prevention of worsening of cardiac function. Boxcar-based AT detection, when triggered by ventricular activity assessment such as ventricular rate stability (VRS) as discussed in this document, may enhance the performance and functionality of an implantable medical device. For example, the VRS trigger may help reduce under-detection of a portion or an entirety of certain AT episodes, thus increasing overall detection sensitivity, while taking the advantage of boxcar-based AT detection such as low computational burden. The present document also refers to efficient methods of detecting onset and termination of an AT episode. More accurate AT diagnostics, such as AT sustainability, AT episode duration, and patient AT burden, may be generated using the systems and methods discussed herein, yet with little to no additional cost or system complexity.

In some examples, existing system performance can be maintained (e.g., high arrhythmia detection sensitivity and specificity, etc.) using lower cost or less obtrusive systems, apparatus, and methods. For example, because the system or device does not require direct sensing of atrial activity, the system complexity and implementation cost may be reduced. It may particularly be beneficial for patient not indicated for atrial lead implantation either for atrial activity sensing or for atrial pacing. Moreover, the arrhythmia detection discussed in this document may make more efficient use of device memory by storing information such as timings of AT onset and termination, which are clinically relevant to treatment and AT patient management. With improved AT detection, fewer alarms are provided, battery life can be extended, fewer unnecessary drugs and procedures may be scheduled, prescribed, or provided, and an overall system cost and power savings may be realized in contrast to existing medical devices and systems.

FIG. 1 illustrates generally an example of a patient management system 100 and portions of an environment in which the system 100 may operate. The patient management system 100 may perform a range of activities, including remote patient monitoring and diagnosis of a disease condition. Such activities can be performed proximal to a patient, such as in the patient's home or office, through a centralized server, such as in a hospital, clinic or physician's office, or through a remote workstation, such as a secure wireless mobile computing device.

The patient management system 100 may include an ambulatory system 105 associated with a patient 102, an external system 125, and a telemetry link 115 providing for communication between the ambulatory system 105 and the external system 125.

The ambulatory system 105 may include an ambulatory medical device (AMD) 110. In an example, the AMD 110 may be an implantable device subcutaneously implanted in a chest, abdomen, or other parts of the patient 102. Examples of the implantable device may include, but are not limited to, pacemakers, pacemaker/defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The AMD 110 alternatively or additionally may include a subcutaneous medical device such as a subcutaneous monitor or diagnostic device, external monitoring or therapeutic medical devices such as automatic external defibrillators (AEDs) or Holter monitors, or wearable medical devices such as patch-based devices, smart watches, or smart accessories.

By way of example, the AMD 110 may be coupled to a lead system 108. The lead system 108 may include one or more transvenously, subcutaneously, or non-invasively placed leads or catheters. Each lead or catheter may include one or more electrodes. The arrangements and uses of the lead system 108 and the associated electrodes may be determined using the patient need and the capability of the AMD 110. The associated electrodes on the lead system 108 may be positioned at the patient's thorax or abdomen to sense a physiologic signal indicative of cardiac activity, or physiologic responses to diagnostic or therapeutic stimulations to a target tissue. By way of example and not limitation, and as illustrated in FIG. 1, the lead system 108 may be surgically inserted into, or positioned on the surface of, a heart 101. The electrodes on the lead system 108 may be positioned on a portion of a heart 101, such as a right atrium (RA), a right ventricle (RV), a left atrium (LA), or a left ventricle (LV), or any tissue between or near the heart portions. In some examples, the lead system 108 and the associated electrodes may alternatively be positioned on other parts of the body to sense a physiologic signal containing information about patient heart rate or pulse rate. In an example, the ambulatory system 105 may include one or more leadless sensors not being tethered to the AMD 110 via the lead system 108. The leadless ambulatory sensors may be configured to sense a physiologic signal and wirelessly communicate with the AMD 110.

The AMD 110 may be configured as a monitoring and diagnostic device. The AMD 110 may include a hermetically sealed can that houses one or more of a sensing circuit, a control circuit, a communication circuit, and a battery, among other components. The sensing circuit may sense a physiologic signal, such as using a physiologic sensor or the electrodes associated with the lead system 108. Examples of the physiologic signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, right ventricular (RV) pressure, left ventricular (LV) coronary pressure, coronary blood temperature, blood oxygen saturation, one or more heart sounds, intracardiac acceleration, physical activity or exertion level, physiologic response to activity, posture, respiration rate, tidal volume, respiratory sounds, body weight, or body temperature.

The AMD 110 may include a physiologic event detector circuit 160 configured to detect a physiologic event using the sensed physiologic signals. In an example, the physiologic event includes a cardiac arrhythmia episode, such as an episode of atrial fibrillation, atrial flutter, atrial tachycardia, supraventricular tachycardia, ventricular tachycardia, or ventricular fibrillation, cardiac pauses, among other brady- or tachy-arrhythmia. In an example, the physiologic event detector circuit 160 is configured to detect syncope, a presyncopal event or a precipitating event that may lead to a full-blown syncope. In some examples, the physiologic event detector circuit 160 is configured to detect worsening of a chronic medical condition, such as worsening heart failure (WHF). The physiologic event detector circuit 160 may execute a detection algorithm to monitor one or more physiologic signals continuously or periodically, and to detect the physiologic event automatically. Additionally or alternatively, the physiologic event detector circuit 160 may be configured to operate in a patient-triggered mode, register a patient-triggered episode and record physiologic data in response to a user-activated trigger. The trigger may be activated by the patient when the patient demonstrates certain signs or symptoms, or experiences a precursor event indicative of a medical event.

The AMD 110 may alternatively be configured as a therapeutic device configured to treat arrhythmia or other heart conditions. The AMD 110 may additionally include a therapy unit that may generate and deliver one or more therapies. The therapy may be delivered to the patient 102 via the lead system 108 and the associated electrodes. The therapies may include electrical, magnetic, or other types of therapy. The therapy may include anti-arrhythmic therapy to treat an arrhythmia or to treat or control one or more complications from arrhythmia, such as syncope, congestive heart failure, or stroke, among others. Examples of the anti-arrhythmic therapy may include pacing, cardioversion, defibrillation, neuromodulation, drug therapies, or biological therapies, among other types of therapies. In an example, the therapies may include cardiac resynchronization therapy (CRT) for rectifying dyssynchrony and improving cardiac function in CHF patients. In some examples, the AMD 110 may include a drug delivery system such as a drug infusion pump to deliver drugs to the patient for managing arrhythmia or complications from arrhythmia.

The external system 125 may include a dedicated hardware/software system such as a programmer, a remote server-based patient management system, or alternatively a system defined predominantly by software running on a standard personal computer or a mobile device. The external system 125 may manage the patient 102 through the AMD 110 connected to the external system 125 via a communication link 115. This may include, for example, programming the AMD 110 to perform one or more of acquiring physiologic data, performing at least one self-diagnostic test (such as for a device operational status), analyzing the physiologic data to detect a cardiac arrhythmia, or optionally delivering or adjusting a therapy to the patient 102. Additionally, the external system 125 may receive device data from the AMD 110 via the communication link 115. Examples of the device data received by the external system 125 may include real-time or stored physiologic data from the patient 102, diagnostic data such as detection of cardiac arrhythmia or events of worsening heart failure, responses to therapies delivered to the patient 102, or device operational status of the AMD 110 (e.g., battery status and lead impedance). The telemetry link 115 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

By way of example and not limitation, the external system 125 may include an external device 120 in proximity of the AMD 110, and a remote device 124 in a location relatively distant from the AMD 110 in communication with the external device 120 via a telecommunication network 122. Examples of the external device 120 may include a programmer device.

The remote device 124 may be configured to evaluate collected patient data and provide alert notifications, among other possible functions. In an example, the remote device 124 may include a centralized server acting as a central hub for collected patient data storage and analysis. The server may be configured as a uni-, multi- or distributed computing and processing system. The remote device 124 may receive patient data from multiple patients including, for example, the patient 102. The patient data, such as medical event episodes, may be collected by the AMD 110, among other data acquisition sensors or devices associated with the patient 102. The remote device 124 may include a storage unit to store the patient data in a patient database. The storage unit may additionally store an association between a plurality of episode characterizations and a plurality of detection algorithms for detecting a medical event having respective episode characterizations. The server may process the device-generated event episodes to verify that a specific medical event (e.g., a cardiac arrhythmia type) is detected such that the device-detected event is a true positive (TP) detection; or that no such medical event is detected such that the device-detected event is a false positive (FP) detection. The processing of the device-generated medical event episodes may be based on a stored association. In an example, a first event episode may be presented to a user (e.g., a clinician), who would provide an adjudication decision and a first episode characterization. If the adjudication decision indicates that the first event episode is a FP detection, then the server may identify from the stored association a detection algorithm corresponding to the first episode characterization, and process a second event episode using at least the identified detection algorithm to determine that the second event episode is either a TP or a FP detection. The server may schedule a presentation of at least a portion of the second episode using the processing result of the second episode. By using the detection algorithms tailored for recognizing episode with an episode characterization associated with a FP episode, more FP episodes having the same or similar episode characterization may be identified, and therefore avoided from being reviewed and adjudicated by the user. If the second event episode is determined to be a TP episode, then an alert is generated indicating further user review may be warranted.

By way of example, alert notifications may include a Web page update, phone or pager call, E-mail, SMS, text or "Instant" message, as well as a message to the patient and a simultaneous direct notification to emergency services and to the clinician. Other alert notifications are possible. In some examples, the server may include a medical event prioritizer circuit configured to prioritize the alert notifications. For example, an alert of a detected medical event may be prioritized using a similarity metric between the physiologic data associated with the detected medical event to physiologic data associated with the historical alerts.

The remote device 124 may additionally include one or more locally configured clients or remote clients securely connected over the network 122 to the server. Examples of the clients may include personal desktops, notebook computers, mobile devices, or other computing devices. Users, such as clinicians or other qualified medical specialists, may use the clients to securely access stored patient data assembled in the database in the server, and to select and prioritize patients and alerts for health care provisioning. The remote device 124, including the server and the interconnected clients, may execute a follow-up scheme by sending follow-up requests to the AMD 110, or by sending a message or other communication to the patient 102, clinician or authorized third party as a compliance notification.

The network 122 may provide wired or wireless interconnectivity. In an example, the network 122 may be based on the Transmission Control Protocol/Internet Protocol (TCP/IP) network communication specification, although other types or combinations of networking implementations are possible. Similarly, other network topologies and arrangements are possible.

One or more of the external device 120 or the remote device 124 may output the detected medical events to a user such as the patient or a clinician, or to a process including, for example, an instance of a computer program executable in a microprocessor. In an example, the process may include an automated generation of recommendations for a therapy, or a recommendation for further diagnostic test or treatment. In an example, the external device 120 or the remote device 124 may respectively include display units for displaying the physiologic or functional signals, or alerts, alarms, emergency calls, or other forms of warnings to signal the detection of arrhythmia. In some examples, the external system 125 may include an external data processor configured to analyze the physiologic or functional signals received by the AMD 110, and to confirm or reject the detection of the medical events. Computationally intensive algorithms, such as machine-learning algorithms, may be implemented in the external data processor to process the data retrospectively to detect cardia arrhythmia.

Portions of the AMD 110 or the external system 125 may be implemented using hardware, software, firmware, or combinations thereof. Portions of the AMD 110 or the external system 125 may be implemented using an application-specific circuit that may be constructed or configured to perform one or more particular functions, or may be implemented using a general-purpose circuit that may be programmed or otherwise configured to perform one or more functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
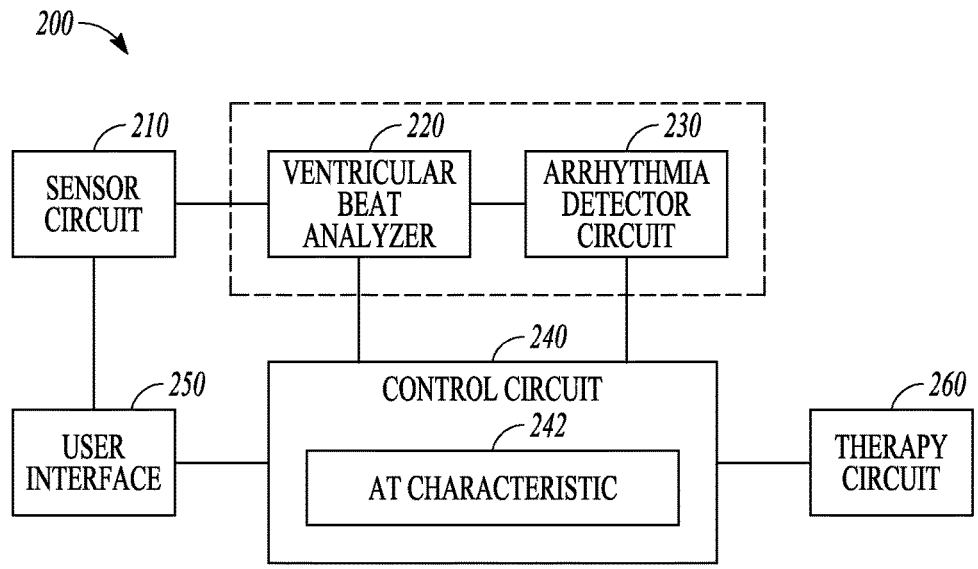
FIG. 2 illustrates generally an example of an arrhythmia detection system configured to detect an arrhythmia episode, such as an AT episode.

FIG. 2 illustrates generally an example of an arrhythmia detection system 200 configured to detect an arrhythmia episode, such as an AT episode. Portions of the arrhythmia detection 200 may be included in the physiologic event detector circuit 160 of the AMD 110. The arrhythmia detection system 200 may include one or more of a sensor circuit 210, a ventricular beat analyzer circuit 220, an arrhythmia detector circuit 230, a controller circuit 240, and a user interface unit 250. The arrhythmia detection system 200 may additionally include an optional therapy circuit 260.

The sensor circuit 210 may include a sense amplifier circuit to sense a physiologic signal from a patient via one or more implantable, wearable, or otherwise ambulatory sensors or electrodes associated with the patient. The sensed physiologic signal may contain information about pulsatile cardiac activity, such as heart rate or pulse rate. Examples of the physiologic signals may include surface electrocardiography (ECG) such as sensed from electrodes on the body surface, subcutaneous ECG such as sensed from electrodes placed under the skin, intracardiac electrogram (EGM) sensed from the one or more electrodes on the lead system 108, thoracic or cardiac impedance signal, arterial pressure signal, pulmonary artery pressure signal, left atrial pressure signal, RV pressure signal, LV coronary pressure signal, coronary blood temperature signal, blood oxygen saturation signal, heart sound signal such as sensed by an ambulatory accelerometer or acoustic sensors, physiologic response to activity, apnea hypopnea index, one or more respiration signals such as a respiration rate signal or a tidal volume signal, brain natriuretic peptide (BNP), blood panel, sodium and potassium levels, glucose level and other biomarkers and bio-chemical markers, among others. The sensor circuit 210 may include one or more other sub-circuits to digitize, filter, or perform other signal conditioning operations on the received physiologic signal.

In some examples, the physiologic signals may be stored in a storage device such as an electronic medical record system. The sensor circuit 210 may retrieve a physiologic signal from the storage device in response to a command signal that is provided by a system user, or automatically generated in response to occurrence of a specific event.

The ventricular beat analyzer circuit 220 may be coupled to the sensor circuit 210 to detect ventricular beats and assess ventricular activity, such as to evaluate ventricular rate stability (VRS) using the physiologic information such as provided by the sensor circuit 210. In an example, the physiologic information includes a cardiac signal representative of ventricular electrical or mechanical activation. The VRS may be computed using a relative difference in ventricular cycle length between cardiac cycles, such as consecutive cardiac cycles, that measured from the cardiac signal, a variance, a standard deviation, a metric derived from a histogram or a statistical distribution of ventricular cycle length over multiple cardiac cycles, among other variability measures or second-order statistics known in the art. In an example, the VRS may be recursively determined and updated on a beat-by-beat basis, as discussed in the following with reference to FIG. 3.

The arrhythmia detector circuit 230 may be configured to detect, in a plurality of predetermined time periods or windows, respective AT indications using segments of the received physiologic signal corresponding to the distinct time periods or windows. The predetermined time periods or windows may be distinct from each other. The signal segments may be generated by applying boxcar functions to the received physiologic signal. A boxcar function is a data window with non-zero portion equal to the distinct time periods. In an example, the time periods have the same duration of T seconds. The duration T can be user programmable, such as via the user interface 250. By way of example and not limitation, the duration T is approximately 2-5 minutes. In an example, the time periods are consecutive in time without overlapping one another. The arrhythmia detector circuit 230 may generated an AT indication every T seconds using the non-overlapped signal segments. In some examples, the control circuit 240 may automatically adjust the duration T using one or more parameters computed from the previous signal segments, such as heart rate or heart rate stability. Examples of the boxcar-based AT indications using consecutive signal segments as defined by boxcar functions are discussed below, such as with reference to FIG. 3.

The arrhythmia detector circuit 230 can detect the AT indications in the respective distinct time periods by analyzing the ventricular activity within the signal segments defined by the boxcar functions. In an example, the arrhythmia detector circuit 230 can detect the AT indication using a ventricular rate variability over the ventricular cycle lengths within the corresponding time period. In another example, the arrhythmia detector circuit 230 can detect the AT indication using signal morphology of ventricular beats within the corresponding time period. Examples of detecting the AT indications in the respective distinct time periods are discussed below, such as with reference to FIG. 3.

The control circuit 240 may controllably initiate AT detection in response to the ventricular beats satisfying a specific condition, and controllably withhold AT detection when the AT indications, such as produced by the arrhythmia detector circuit 230, satisfy an exit criterion. In an example, the control circuit 240 may monitor the VRS, and trigger the arrhythmia detector circuit 230 to detect respective AT indications within the distinct time periods when the VRS satisfies an instability criterion indicating unstable ventricular rate. At the time of the triggered activation of the arrhythmia detector circuit 230, the monitoring the VRS can be temporarily suspended. Then, according to the detected AT indication in one time period, the control circuit 240 may control the arrhythmia detector circuit to continue to determine an AT indication in a subsequent time period if AT is determined to be present in the current time period, or to withhold detection of AT indication in the subsequent time period if the AT indication detected from current time period satisfies an exit criterion, such as no AT being present in the current time period. When the AT detection is withheld, the control circuit 240 may trigger the ventricular beat analyzer circuit 220 to resume evaluation of ventricular activity, such as evaluating the VRS.

The instability criterion determines a transition from ventricular beat analysis (e.g., VRS monitoring) to boxcar-based AT detection. The instability criterion may be determined using a patient medical condition. In an example, the instability criterion includes a time duration for evaluating the VRS. The ventricular beat analyzer circuit 220 may determine the time duration for evaluating the VRS using a patient medical condition. For example, if the patient has a medical history of syncope, a longer time duration of approximately 10 minutes may be used to evaluate the VRS. On the other hand, if the patient has a medical history of cryptogenic stroke, a shorter time duration such as approximately two minutes may be used to evaluate the VRS.

In some examples, in addition to or in lieu of the VRS as discussed above for triggering the boxcar-based AT detection, the ventricular beat analyzer circuit 220 may be configured to generate one or more physiologic features other than the VRS. The control circuit 240 may trigger the arrhythmia detector circuit 230 to detect respective AT indications within the distinct time periods using one or more said physiologic features. Examples of such physiologic features may include a ventricular rate, a ventricular activation pattern, a ventricular signal morphology, or a cardiac event between consecutive ventricular beats.

The control circuit 240 may generate an AT characteristic 242 using the AT indications detected from the plurality of distinct time periods. In some examples, the control circuit 240 may detect an onset and/or a termination of a sustained AT episode using the boxcar-based AT detections in the plurality of time periods, an example of which is to be discussed in the following with reference to FIG. 4. Other examples of the AT characteristics 242 may include AT duration, AT burden, or other characteristics of the AT episode. The control circuit 240 can store in a memory circuit portions of the received physiologic information, such as the signal segments corresponding to the AT indications indicating a presence of AT. In another example, a portion of the received physiologic information between the detected onset and the detected termination of the AT episode can be stored in the memory circuit.

As illustrated in FIG. 2, the ventricular beat analyzer circuit 220, the arrhythmia detector circuit 230, and the control circuit 240 may respectively include circuit sets comprising one or more other circuits or sub-circuits. The circuits or sub-circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

In various examples, portions of the functions of the ventricular beat analyzer circuit 220, the arrhythmia detector circuit 230, and the control circuit 240 may be implemented as a part of a microprocessor circuit. The microprocessor circuit may be a dedicated processor such as a digital signal processor, application specific integrated circuit (ASIC), microprocessor, or other type of processor for processing information including the physiologic signals received from the sensor circuit 210. Alternatively, the microprocessor circuit may be a general-purpose processor that may receive and execute a set of instructions of performing the functions, methods, or techniques described herein.

The user interface unit 250 may include an input device and an output device. In an example, at least a portion of the user interface unit 250 may be implemented in the external system 130. The input device may receive a user's programming input, such as parameters for adjusting detection criterion and parameters for detecting cardiac arrhythmia. The input device may include a keyboard, on-screen keyboard, mouse, trackball, touchpad, touch-screen, or other pointing or navigating devices. The input device may enable a system user to program the parameters used for sensing the physiologic signals, detecting the arrhythmias, and generating alerts, among others.

The output device may generate a human-perceptible presentation of the detected cardiac arrhythmia. The output device may include a display for displaying the sensed physiologic signal, intermediate measurements or computations such as VRS, AT indications in respective time durations, among others. The output unit may include a printer for printing hard copies of the detection information. The information may be presented in a table, a chart, a diagram, or any other types of textual, tabular, or graphical presentation formats. The presentation of the output information may include audio or other media format to alert the system user of the detected arrhythmic events. In an example, the output device may generate alerts, alarms, emergency calls, or other forms of warnings to signal the system user about the detected arrhythmic events.

The optional therapy circuit 260 may be configured to deliver a therapy to the patient in response to the detected cardiac arrhythmia, such as an AT episode. Examples of the therapy may include electrostimulation therapy delivered to the heart, a nerve tissue, other target tissues, a cardioversion therapy, a defibrillation therapy, or drug therapy. In some examples, the therapy circuit 260 may modify an existing therapy, such as adjust a stimulation parameter or drug dosage.

Figure 3:
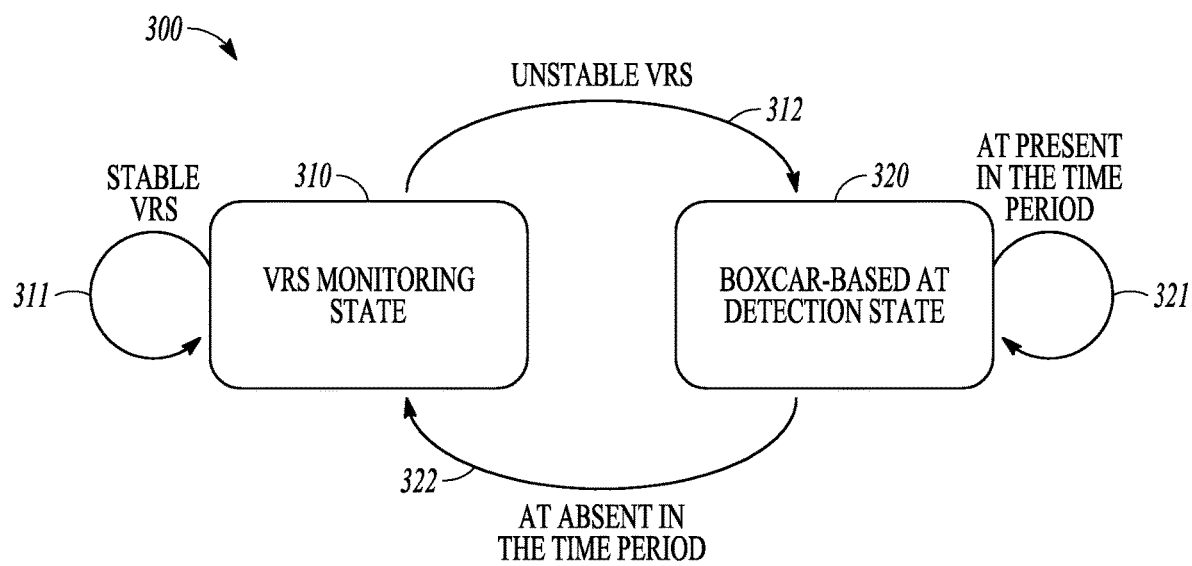
FIG. 3 is a graph illustrating conceptually a state machine including a ventricular rate stability (VRS) monitoring state, a boxcar-based AT detection state, and transitions between said states.

FIG. 3 is a graph illustrating conceptually a state machine 300 including a VRS monitoring state 310 and a boxcar-based AT detection state 320, and transitions between said states. The state machine can be implemented and operate in at least a portion of the system 200, or be implemented in a microprocessor configured to execute instructions to achieve the functions described herein.

The VRS monitoring state 310, which may be executed by the ventricular beat analyzer circuit 220, involves VRS evaluation and comparison against an instability criterion. In an example, the VRS may be computed using ventricular rates or cardiac cycle lengths measured form an electrophysiological signal, such as an ECG, a subcutaneous ECG, or an intracardiac EGM. Alternatively, ventricular rate may be detected using a mechano-physiological signal, such as a heart sound signal sensed using an accelerometer or a microphone sensor, cardiac or thoracic impedance signal, or a blood pressure signal, among other sensors. The VRS may be computed using a standard deviation, a variance, a range (e.g., a difference between minimum and maximum, an interquartile range between upper and lower quartiles, a difference between $10^{th}$ to $90^{th}$ percentiles or other ranges), or other measures of spread of a plurality of ventricular rate or ventricular cycle lengths.

In an example, the VRS may be determined using a count of unstable cardiac cycles ($N_{Unstable}$) within a specific time period or a specific number of cardiac cycles. A cardiac cycle (e.g., cardiac cycle "n") is unstable if a cycle length difference ($\Delta CL$) between the cardiac cycle "n" and a preceding cardiac cycle such as the immediate previous cardiac cycle "n−1", exceeds a CL threshold ($CL_{TH}$). In an example, the $CL_{TH}$ is approximately 80 milliseconds. Alternatively, the cardiac cycle "n" is unstable if the corresponding heart rate (HR(n)=60/CL(n)) differs from the heart rate of a preceding cardiac cycle (HR(n−1)=60/CL(n−1)) exceeds a HR threshold ($HR_{TH}$). In an example, the $HR_{TH}$ is approximately 5 beats per minute (bpm). The formulae below can be used to determine if the cardiac cycle CL(n) is unstable:

$$\Delta CL = |CL(n) - CL(n-1)| > CL_{TH} \quad (1)$$

$$\Delta HR = |HR(n) - HR(n-1)| > HR_{TH} \quad (2)$$

The VRS, such as the number ($N_{Unstable}$) of unstable cardiac cycles determined by the control circuit 240, may be compared to an instability criterion to determine whether the ventricular rate is unstable. Unstable ventricular rate is detected if the $N_{Unstable}$ exceeds a count threshold ($N_{TH}$) or a relative count threshold (% $N_{TH}$). In an example, the VRS indicates an unstable ventricular rate if 80% or more of the ventricular rates or cardiac cycles evaluated are unstable.

In an example, the VRS may be evaluated on a beat-by-beat basis, and adaptively updated when a new ventricular beat is detected. The adaptive update of VRS may be carried out using a cycle length difference ($\Delta CL$) between the present cardiac cycle "n" and a preceding cardiac cycle, such as the immediate previous cardiac cycle "n−1": $\Delta CL(n) = |CL(n) - CL(n-1)|$. Alternatively, the adaptive update of VRS may be based on a HR difference: $\Delta HR = |HR(n) - HR(n-1)|$. Equations (3) and (4) below provide alternative methods of adaptive update of VRS:

$$VRS(n) = a * VRS(n-1) + b * \Delta CL(n) \quad (3)$$

$$VRS(n) = a * VRS(n-1) + b * \Delta HR(n) \quad (4)$$

The weight factors "a" and "b" can be user-programmable scalars. In an example, the ventricular beat analyzer circuit 220 may be configured to initialize the VRS (e.g., VRS(0)) using a variability measure of cycle lengths of a plurality of cardiac cycles. The adaptively updated VRS may be compared to an instability criterion, such as a VRS threshold $VRS_{TH}$, to determine whether the ventricular rate is unstable. The control circuit 240 may determine that an unstable ventricular rate is indicated if the adaptively updated VRS exceeds the $VRS_{TH}$. In an example, $VRS_{TH}$ corresponding to Equation (4) above is approximately 5 bpm.

The boxcar-based AT detection state 320, which may be executed by the arrhythmia detector circuit 230, involves detecting an AT indication using a ventricular rate variability over the ventricular cycle lengths within consecutive time periods, or the boxcar functions. An AT indication is detected if the ventricular rate variability exceeds a specific threshold. In another example, and AT indication involves signal morphology. An AT indication may be detected if a similarity metric between morphological features taken from a signal segment during the time periods and a morphology template falls within a specified range relative to a patient-specific similarity threshold. The morphology template includes morphological features taken from patient baseline physiologic signal, such as sensed during a sinus rhythm. Examples of the similarity measure may include a correlation or a distance in a signal feature space.

In various examples, AT indications may be detected within the respective time periods using a statistical measure of ventricular rate or ventricular cycle length. One example of the statistical measure includes a ventricular rate pattern of consecutive decrease in ventricular rate. The ventricular rate pattern includes a pair of consecutive ventricular rate changes. Both ventricular rate changes are negative, referred to as a "double decrement" ventricular rate pattern. A double-decrement ratio, which represents a prevalence of the double decrement ventricular rate pattern over a specified time period or over a plurality of ventricular beats, may be computed, and used to detect AT (e.g., AF), or to distinguish AT from ectopic beats. The arrhythmia detector circuit 230 may determine a count of double-decrement beat pattern, or a double-decrement ratio. Such a baseline double-decrement pattern of ventricular rate may distinguish frequent premature ventricular contractions (PVCs) from an AT event, because PVCs alone typically do not produce double decrement patterns in ventricular rate. Krueger et al. U.S. patent application Ser. No. 14/825,669, entitled "ATRIAL FIBRILLATION DETECTION USING VENTRICULAR RATE VARIABILITY," refers to double decrement pattern in ventricular heart rate and its use in atrial arrhythmia detection, the disclosure of which is incorporated by reference herein in its entirety.

Another example of the statistical measure includes a ventricular rate cluster, represented by a statistical distribution or a histogram of ventricular rate or cycle length over multiple cardiac cycles. The ventricular rate cluster indicates regularity of ventricular rates of cardiac cycle lengths. Patients with AF are typically presented with irregular ventricular rate variations. However, premature atrial contractions (PACs) may occur at irregular intervals. When PACs conduct to the ventricle, they may produce irregular ventricular rates, resulting in different ventricular clusters than AF. As such, the ventricular rate clusters may be used to distinguish frequent PACs from an AF event. Perschbacher et al. U.S. patent application Ser. No. 15/864,953 entitled "ATRIAL FIBRILLATION DISCRIMINATION USING HEART RATE CLUSTERING," refers to histogram clusters of ventricular rates and their use in discriminating between AF and non-AF events, the disclosure of which is incorporated by reference herein in its entirety.

Yet another example of the statistical measure includes a metric representing the occurrence of various beat patterns of the cycle lengths or heart rates. For example, the beat pattern may include a number or percentage of consecutive heart beats with each time period (e.g., a 2-minute time windows) that are within +/−5 bpm. In an example, the statistical measure includes an atrioventricular (AV) conduction block metric indicating a presence or degree of conduction abnormality during a sinus rhythm, such as a Wenckebach score representing the prevalence of Wenckebach block over a time period. Examples of the Wenckebach detector may be based on a repetitiveness indictor of various beat patterns of the cycle lengths or heart rates, such as discussed in Perschbacher et al. U.S. patent application Ser. No. 15/786,824 entitled "SYSTEMS AND METHODS FOR ARRHYTHMIA DETECTION," the disclosure of which is incorporated by reference herein in its entirety. Other examples of the statistical measure may include a signal morphology metric representing regularity of ventricular depolarization signal morphology during sinus rhythm, or a signal quality metric such as a signal-to-noise (SNR). The signal quality or signal morphology indicator may differentiate the AF from noise.

The state machine 300 also includes transitions between the VRS monitoring state 310 and the boxcar-based AT detection state 320 when certain conditions are met. The transition from the VRS monitoring state 310 to the boxcar-based AT detection state 320 can be determined by the instability criterion. If the VRS does not satisfy the instability criterion (e.g., less than 80% of the ventricular rates or cardiac cycles evaluated are unstable as defined in formula (1) or (2), or if the adaptively updated VRS according to Equation (4) is less than 5 bpm), then no state transition occurs; and the VRS monitoring 311 continuous. If VRS satisfies the instability criterion (e.g., 80% or more of the ventricular rates or cardiac cycles evaluated are unstable, or if the adaptively updated VRS according to Equation (4) is equal to or greater than 5 bpm), then the VRS monitoring process is suspended; and a transition 312 to boxcar-based AT detection state 320 occurs. The arrhythmia detector circuit 230 detects an AT indication in a time period defined by a boxcar function. If the AT indication detected from the present time period indicates a presence of AT, the AT detection process 321 continuous, and a subsequent signal segment is analyzed to detect presence or absence of an AT indication. However, if no AT event is detected from the present time period, then the AT detection process is withheld in the subsequent time period; and a transition 322 to the VRS monitoring state 310 occur such that the process of VRS evaluation against instability criterion resumes.

Figure 4:
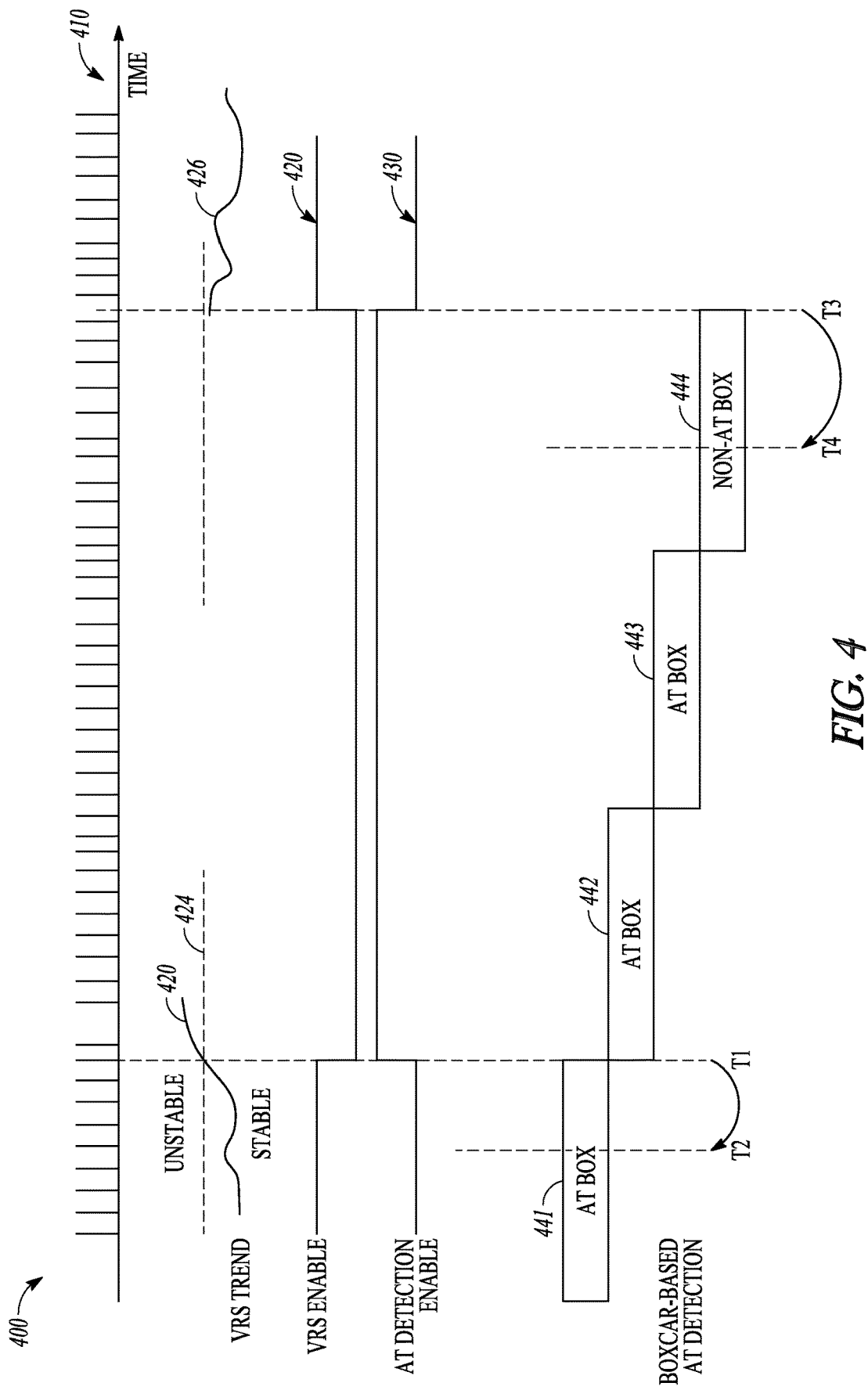
FIG. 4 is a timing diagram illustrating event timing associated with VRS monitoring and boxcar-based AT detection in respective time periods.

FIG. 4 is a timing diagram 400 illustrating event timing associated with VRS monitoring and boxcar-based AT detection in respective time periods, such as illustrated in FIG. 3. The control circuit 240 may control the event timing, and maintain two control signals including a VRS enable signal 420 and a boxcar-based AT detection signal 430. A cardiac signal 410 that contains information of ventricular beats is used for ventricular rate analysis and AT detection. The VRS monitoring state is enabled, the VRS is evaluated and trended over time, and the boxcar-based AT detection is suspended. At time T1, the VRS trend 422 exceeds a VRS threshold 424 (e.g., the unstable beat count threshold % $N_{TH}$ of 80%, or the $VRS_{TH}$ of 5 bpm), indicating unstable ventricular rate being detected. The VRS monitoring process is suspended, and the boxcar-based AT detection is initiated. The control circuit 240 may retrospectively determine a first time period (i.e., a first boxcar) 441 that precedes T1. The first time period 441 has a specified duration, such as 2 minutes in an example. The arrhythmia detector circuit 230 may detect a first AT indication in the first time period 441 using ventricular rate variability, signal morphology, or one or more statistical measures of ventricular rate or ventricular cycle length, such as a ventricular rate pattern, ventricular rate cluster, or Wenckebach score, as discussed above with reference to FIG. 3. Additionally, the arrhythmia detector circuit 230 may detect an AT onset and the corresponding timing T2 during the first time period 441, such as based on a degree of change or rate of change in ventricular rate variability, signal morphology, or a statistical measure of ventricular rate or ventricular cycle length.

In the illustrated example, the first AT indication indicates that AT is present in the first time period 441. A signal segment in a subsequent second time period 442 is then analyzed to generate a second AT indication, which indicates a presence of AT in the second time period 442. Then, a signal segment in a subsequent third time period 443 is analyzed to generate a third AT indication, which also indicates a presence of AT in the third time period 443. Then, a signal segment in a subsequent fourth time period 444 is analyzed to generate a fourth AT indication, which indicates that no AT is detected in the fourth time period 444. At the end of the fourth time period 444 (i.e., at time T3), the boxcar-based AT detection process is disabled, and the VRS monitoring is enabled to evaluate and generate the VRS 426. The arrhythmia detector circuit 230 may detect an AT termination and the corresponding timing T4 during the fourth time period 444, such as based on a degree of change or rate of change in ventricular rate variability, signal morphology, or a statistical measure of ventricular rate or ventricular cycle length. Based on the AT detection indications in the time durations 441-444, the control circuit 240 may generate an AT characteristic, such as a duration of a sustained AT episode that begins at T2 and ends at T4. The AT duration may be used to determine patient AT burden, such as within a 24-hour period.

Figure 5:
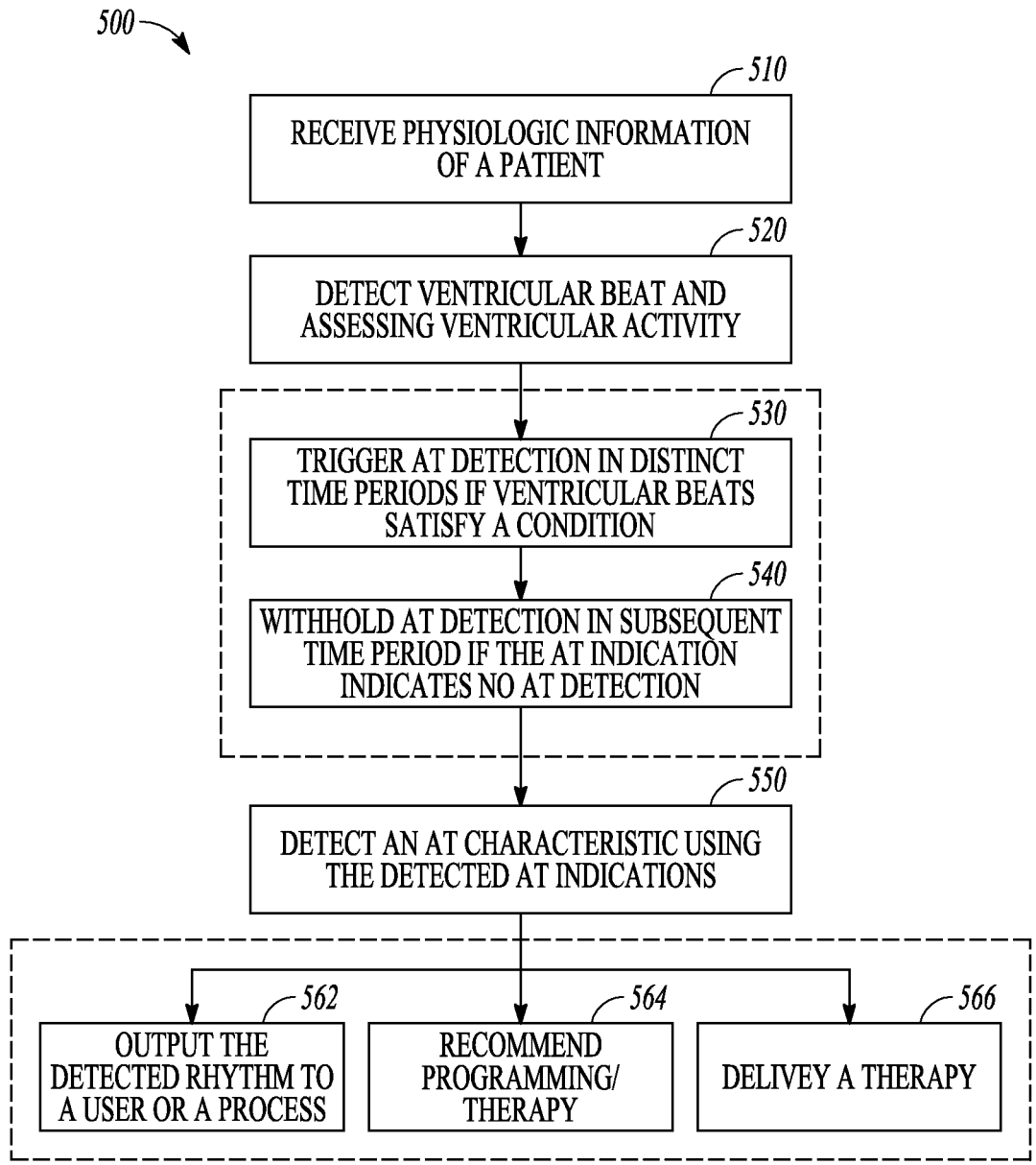
FIG. 5 is a flowchart illustrating an example of a method for detecting cardiac arrhythmia such as an AT episode.

FIG. 5 is a flowchart illustrating an example of a method 500 for detecting cardiac arrhythmia in a patient, such as AT episode. Examples of AT that can be detected using the method 500 may include atrial fibrillation (AF), atrial flutter (AFL), atrial tachycardia, paroxysmal supraventricular tachycardia (PSVT), among others. The method 500 may be implemented and executed in an ambulatory medical device such as an implantable or wearable device, or in a remote patient management system. In an example, the method 500 may be implemented in and executed by the cardiac arrhythmia detection circuit 160 in the AMD 110, the external system 130, or the arrhythmia detection system 200.

The method 500 commences at step 510, where physiologic information of a patient may be received. The physiologic information may include physiologic signals sensed by one or more implantable, wearable, or otherwise ambulatory sensors. Examples of the physiologic signals may include cardiac electrical signals, such as ECG or EGM, or signals indicative of cardiac mechanical activity, such as pressure, impedance, heart sounds, or respiration signals. The sensed physiologic signal may be pre-processed, including amplification, digitization, filtering, or other signal conditioning operations. In some examples, patient physiologic signals may be sensed and stored in a storage device, such as an electronic medical record system, and retrieved for use such as according to the method 500.

At 520, ventricular beats may be detected and ventricular activity assessed such as using the ventricular beat analyzer circuit 220. In an example, ventricular activity assessment may include evaluation of ventricular rate stability (VRS). The VRS may be computed using a relative difference in ventricular cycle length between cardiac cycles measured from the cardiac signal. The VRS may alternatively be computed using variance, standard deviation, a metric derived from a histogram or a statistical distribution of ventricular cycle length over multiple cardiac cycles, or other variability measures or second-order statistics known in the art. In an example, the VRS may be recursively determined and updated on a beat-by-beat basis each time a ventricular beat is detected, as discussed in the following with reference to FIG. 3.

At 530, AT detection may be triggered in response to ventricular beats satisfying a specific condition. In an example, the AT detection may be triggered when the VRS satisfies an instability criterion. In another example, the AT detection may be triggered by physiologic features other than the VRS, such as a ventricular rate, a ventricular activation pattern, a ventricular signal morphology, or a cardiac event between consecutive ventricular beats. The AT detection includes detecting AT indications in a plurality of distinct time periods, using segments of the received physiologic signal corresponding to the distinct time periods. In an example, the time periods may have the same duration, such as approximately 2-5 minutes. In an example, the time periods are consecutive in time without overlapping one another. Detection of AT indications in the respective distinct time periods may be performed using the arrhythmia detector circuit 230, and includes analyzing the ventricular rate variability within the signal segments defined by the boxcar functions. In another example, detection of AT indication may be based on signal morphology of ventricular beats within the corresponding time periods. In some examples, detection of AT indication may involve one or more statistical measures of ventricular rate or ventricular cycle length, such as a ventricular rate pattern, ventricular rate cluster, or Wenckebach score, as discussed above with reference to FIG. 3.

At 540, if the AT indication indicates that no AT is detected in one of the distinct time periods, then the AT detection process can be withheld in a time period subsequent to the present time period. When the AT detection process is suspended, the ventricular beat detection and ventricular activity assessment may be resumed. However, if the AT indication indicates that AT is present in the time period, then the AT detection process can be continued; and a next AT indication may be generated in a subsequent time period. Initiation or continued AT detection and suspension of AT detection in steps 530-540 can be carried out using the control circuit 240.

At 550, an AT characteristic may be determined using the detected AT indications corresponding to the multiple distinct time periods. Examples of the AT characteristics may include an onset and/or a termination of a sustained AT episode, such as to be discussed in FIG. 6 below. Other examples of the AT characteristics may include AT duration, AT burden, or other characteristics of the AT episode. Portions of the received physiologic information, such as the signal segments corresponding to the AT indications indicating a presence of AT, may be stored in a memory.

The determined AT characteristic may be provided to one or more processes 552, 554, or 556. At 552, the AT characteristic may be output to a user or a process, such as via an output device of the user interface 250. In an example, the detected AT episode (e.g., from the detected AT onset to termination) may be displayed on a display unit, including the sensed physiologic signal, VRS that triggered the AT detection, and other AT detection information (e.g., ventricular rate variability, morphology, or one or more statistical measures of ventricular rate or ventricular cycle length). Hard copies of the detection information may be generated. In various examples, alerts, alarms, emergency calls, or other forms of warnings may be generated to signal the system user about the detected arrhythmic episode.

At 554, a recommendation may be generated and provided to a user. The recommendation may include one or more of further diagnostic tests to be performed, anti-arrhythmic therapy to treat the detected arrhythmia or to alleviate the arrhythmic complications. The recommendation may include adjustment of one or more arrhythmia detection parameters, such as the instability criterion (e.g., threshold values) associated with the VRS or other physiologic features for triggering the AT detection process, parameters used for generating AT indications within the distinct time periods, or the exit criterion for withholding the AT detection process. The method 500 may include the optional step 556 of delivering a therapy to the patient in response to the detected AT episode, such as via the optional therapy circuit 260 as illustrated in FIG. 2. Examples of the therapy may include electrostimulation therapy delivered to the heart, a nerve tissue, other target tissues, a cardioversion therapy, a defibrillation therapy, or drug therapy including delivering drug to a tissue or organ. In some examples, an existing therapy or treatment plan may be modified to treat the detected arrhythmia.

Figure 6:
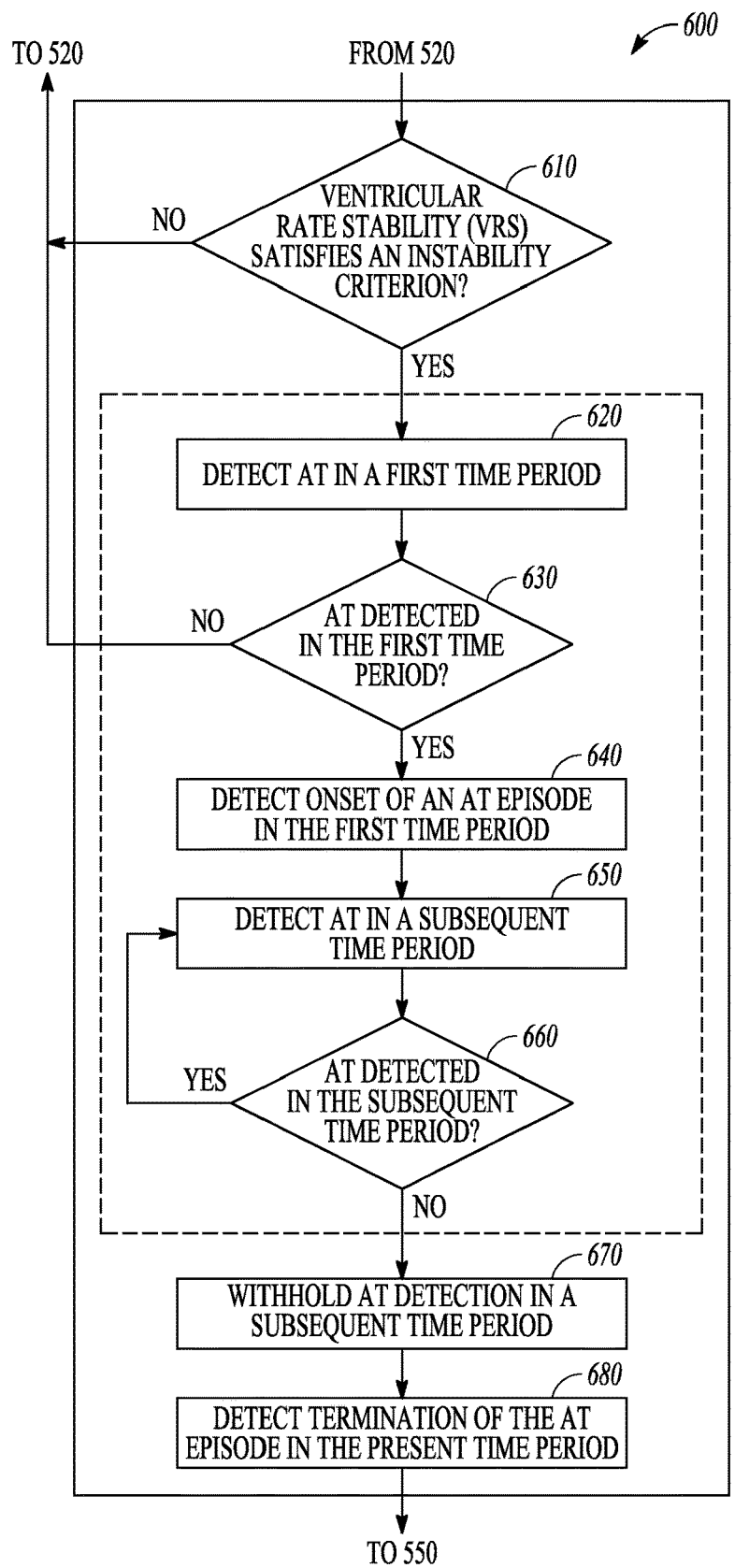
FIG. 6 is a flowchart illustrating an example of a method for detecting an AT episode using a triggered AT detection in multiple distinct time periods.

FIG. 6 is a flowchart illustrating an example of a method 600 of detecting an AT episode using a triggered AT detection in multiple distinct time periods, hereinafter also referred to as a boxcar-based AT detection. The method 600 represents an embodiment of a portion of the method 500, such as steps 530-540, and may be implemented in and executed by the system 200.

The boxcar-based AT detection may be triggered by ventricular rate stability (VRS). That is, the ventricular activity assessment at 520 may include an evaluation of VRS using the detected ventricular beats. The VRS may be evaluated on a beat-by-beat basis, and determined using one of the Equations (1)-(4) as discussed above. At 610, the VRS can be compared to an instability criterion, such as a threshold. If the VRS does not satisfy the instability criterion (e.g., less than 80% of the ventricular rates or cardiac cycles evaluated are unstable as defined in formula (1) or (2), or if the adaptively updated VRS according to Equation (4) is less than 5 bpm), then ventricular activity assessment such as VRS monitoring process continuous at 520. If at 610 the VRS satisfies the instability criterion (e.g., 80% or more of the ventricular rates or cardiac cycles evaluated are unstable, or if the adaptively updated VRS according to Equation (4) is equal to or greater than 5 bpm), then the VRS monitoring process is suspended; and a boxcar-based AT detection process commences. At 620, AT detection can be performed in a first time period, such as using ventricular rate variability, signal morphology, or one or more statistical measures of ventricular rate or ventricular cycle length, such as a ventricular rate pattern, ventricular rate cluster, or Wenckebach score, as discussed above with reference to FIG. 3. The first time period can be retrospective in time, that is, it precedes the time instant when the VRS exceeds a VRS threshold, such as the example illustrated in FIG. 4.

If at 630 no AT event is detected in the first time period, then the AT detection process is withheld, and the ventricular activity assessment such as VRS monitoring process continuous at 520. If at 630 the AT is detected in the first time period, then at 640, an AT onset, and the corresponding timing of the AT onset, can be detected, such as based on a degree of change or rate of change in ventricular rate variability, signal morphology, or a statistical measure of ventricular rate or ventricular cycle length. At 650, AT detection can proceed to a subsequent second time period, and a corresponding AT indication may be generated in the second time period such as using an AT detection method similar to that used in the first time period at 620. If at 660 the second AT indication indicates a presence of AT, then the AT detection process continues to a subsequent third time period. The boxcar-based AT detection can continue until at 660 the AT indication satisfies an exit criterion, such as no AT is detected in the present time period. Then at 670 the AT detection is withheld in a subsequent time period. At 680, an AT termination and the corresponding timing for the AT termination may be determined, such as based on a degree of change or rate of change in ventricular rate variability, signal morphology, or a statistical measure of ventricular rate or ventricular cycle length. Based on the AT detection indications in the multiple distinct time durations, an AT characteristic, such as an AT duration between the detected AT onset and AT termination, may be determined at 550. The AT duration may be used to determine patient AT burden, such as within a 24-hour period.

Figure 7:
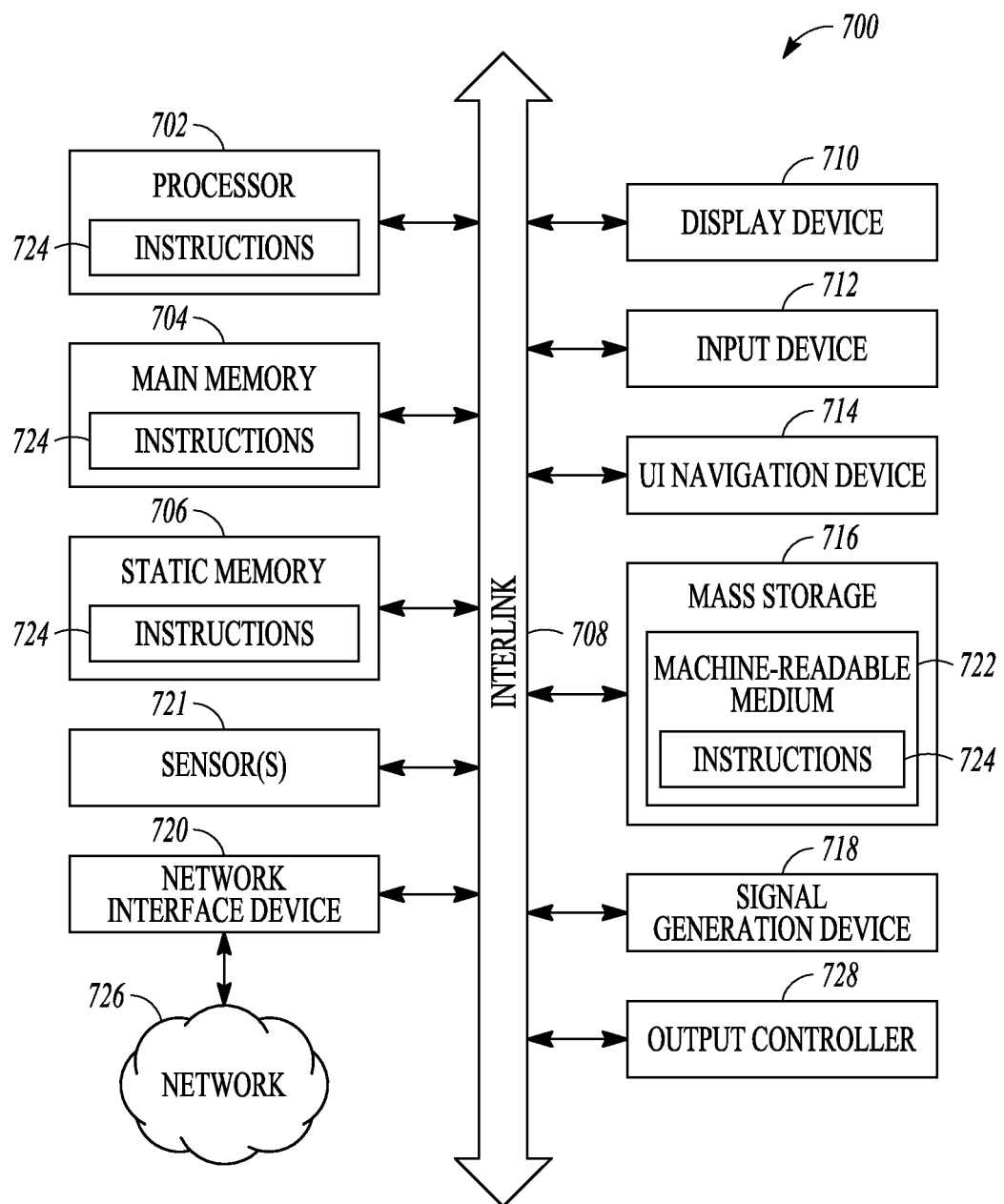
FIG. 7 illustrates generally a block diagram of an example machine upon which any one or more of the techniques (e.g., methodologies) discussed herein may perform.

FIG. 7 illustrates generally a block diagram of an example machine 700 upon which any one or more of the techniques (e.g., methodologies) discussed herein may perform. Portions of this description may apply to the computing framework of various portions of the LCP device, the IMD, or the external programmer.

In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 700 may include a hardware processor 702 (e.g., a central processing unit (CPU), a graphics processing unit (GPU), a hardware processor core, or any combination thereof), a main memory 704 and a static memory 706, some or all of which may communicate with each other via an interlink (e.g., bus) 708. The machine 700 may further include a display unit 710 (e.g., a raster display, vector display, holographic display, etc.), an alphanumeric input device 712 (e.g., a keyboard), and a user interface (UI) navigation device 714 (e.g., a mouse). In an example, the display unit 710, input device 712 and UI navigation device 714 may be a touch screen display. The machine 700 may additionally include a storage device (e.g., drive unit) 716, a signal generation device 718 (e.g., a speaker), a network interface device 720, and one or more sensors 721, such as a global positioning system (GPS) sensor, compass, accelerometer, or other sensors. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 716 may include a machine readable medium 722 on which is stored one or more sets of data structures or instructions 724 (e.g., software) embodying or utilized by any one or more of the techniques or functions described herein. The instructions 724 may also reside, completely or at least partially, within the main memory 704, within static memory 706, or within the hardware processor 702 during execution thereof by the machine 700. In an example, one or any combination of the hardware processor 702, the main memory 704, the static memory 706, or the storage device 716 may constitute machine-readable media.

While the machine-readable medium 722 is illustrated as a single medium, the term "machine readable medium" may include a single medium or multiple media (e.g., a centralized or distributed database, and/or associated caches and servers) configured to store the one or more instructions 724.

The term "machine readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may further be transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802. 11 family of standards known as WiFi®, IEEE 802. 16 family of standards known as WiMax®), IEEE 802. 15. 4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A system for detecting atrial tachyarrhythmia (AT), comprising:
   a ventricular beat analyzer circuit configured to receive physiologic information of a patient and to detect ventricular beats using the received physiologic information;
   an arrhythmia detector circuit configured to detect respective AT indications in distinct time periods using portions of the received physiologic information during the distinct time periods; and
   a control circuit configured to:
   monitor the ventricular beats on a beat-by-beat basis;
   in response to the ventricular beats satisfying an instability criterion indicative of unstable ventricular rate, trigger the arrhythmia detector circuit to detect the respective AT indications in distinct time periods using a stability of ventricular beats in the distinct time periods, and determine an AT characteristic using the detected respective AT indications; and in response to an AT indication indicating an absence of AT in one of the distinct time periods, control the arrhythmia detector circuit to withhold detecting AT indication in a time period subsequent to the one of the distinct time periods, and trigger the ventricular beat analyzer to monitor and analyze additional ventricular beats.

2. The system of claim 1, wherein:
the stability of ventricular beat includes a ventricular rate stability (VRS) of the detected ventricular beats; and
the distinct time periods for detecting respective AT indications include a time period preceding in time a determination of the VRS satisfying the instability criterion.

3. The system of claim 2, wherein the control circuit is configured to:
trigger the arrhythmia detector circuit to detect a first AT indication during a first time period in response to the VRS satisfying the instability criterion;
if the first AT indication indicates a presence of AT in the first time period, control the arrhythmia detector circuit to detect a second AT indication during a subsequent second time period; and
if the first AT indication indicates an absence of AT in the first time period, control the arrhythmia detector circuit to withhold detection of the second AT indication during the subsequent second time period, and trigger the ventricular beat analyzer circuit to evaluate the VRS.

4. The system of claim 3, wherein the control circuit is further configured to:
if the second AT indication indicates a presence of AT in the second time period, control the arrhythmia detector circuit to detect a third AT indication during a third time period subsequent to the second time period;
if the second AT indication indicates an absence of AT in the second time period, control the arrhythmia detector circuit to withhold detection of the third AT indication, and trigger the ventricular beat analyzer circuit to evaluate the VRS; and
determine an AT characteristic using one or more the first, second, or third AT indication.

5. The system of claim 3, wherein the control circuit is configured to determine the first time period that precedes a time of determining the VRS satisfying the instability criterion.

6. The system of claim 3, wherein the arrhythmia detector circuit is configured to detect the AT characteristic including detecting one or more of:
an onset of an AT episode using the received physiologic information during the first time period; or
a termination of the AT episode using the received physiologic information during the second time period, if the second AT indication indicates an absence of AT in the second time period.

7. The system of claim 6, wherein the arrhythmia detector circuit is configured to detect the AT characteristic including a duration of the AT episode from the detected onset to the detected offset of the AT episode.

8. The system of claim 2, wherein:
the ventricular beat analyzer circuit is configured to evaluate the VRS using a count of unstable cardiac cycles within a specific time period or a specific number of cardiac cycles, the unstable cardiac cycle corresponding to a cycle length difference from a preceding cycle length exceeding a threshold; and the control circuit is configured to determine that the VRS indicates an unstable ventricular rate if the count of unstable cardiac cycles exceeds a count threshold.

9. The system of claim 2, wherein:
the ventricular beat analyzer circuit is configured to initialize the VRS using a variability measure of cycle lengths of a plurality of cardiac cycles, and to adaptively update the VRS using a cycle length difference between a present cycle length and a preceding cycle length; and
the control circuit is configured to determine that the VRS indicates an unstable ventricular rate if the adaptively updated VRS exceeds a threshold value.

10. The system of claim 1, wherein the distinct time periods are consecutive time periods, and the arrhythmia detector circuit is configured to detect the respective AT indications using one or more of ventricular rate variability or ventricular signal morphology within the distinct time periods.

11. The system of claim 10, wherein the arrhythmia detector circuit is configured to:
determine a count of unstable cardiac cycles within a specific time period, the unstable cardiac cycle corresponding to a cycle length difference from a preceding cycle length exceeding a threshold; and
detect the AT indication indicating a presence of AT in the specific time period if the count of unstable cardiac cycles exceeds a threshold count.

12. The system of claim 1, wherein:
the ventricular beat analyzer circuit is configured to generate a physiologic feature including one or more of a ventricular rate, a ventricular activation pattern, a ventricular signal morphology, or a cardiac event between consecutive ventricular beats; and
the control circuit is configured to trigger the arrhythmia detector circuit to detect the respective AT indications in response to the generated physiologic feature satisfying a condition.

13. The system of claim 1, comprising a therapy circuit configured to initiate or adjust a therapy according to the determined AT characteristic.

14. A method for detecting atrial tachyarrhythmia (AT), comprising:
receiving physiologic information of a patient;
detecting ventricular beats and assessing ventricular activity using the received physiologic information via a ventricular beat analyzer circuit;
monitoring the ventricular beats on a beat-by-beat basis, and in response to the detected ventricular beats satisfying a specific condition, triggering detection of respective AT indications in distinct time periods using stability of ventricular beats in the distinct time periods via an arrhythmia detector circuit;
in response to an AT indication indicating an absence of AT in one of the distinct time periods, withholding detection of AT indication in a time period subsequent to the one of the distinct time periods, and re-assessing ventricular activity via the ventricular beat analyzer; and
generating an AT characteristic using the detected respective AT indications.

15. The method of claim 14, wherein:
assessing the ventricular activity incudes evaluating a ventricular rate stability (VRS) using the detected ventricular beats; and triggering detection of respective AT indications in distinct time periods is in response to the VRS satisfying an instability criterion indicative of unstable ventricular rate.

16. The method of claim 15, comprising:
triggering detection of a first AT indication during a first time period in response to the VRS satisfying the instability criterion;
if the first AT indication indicates a presence of AT in the first time period, detecting a second AT indication during a subsequent second time period; and
if the first AT indication indicates an absence of AT in the first time period, withholding detection of the second AT indication during the subsequent second time period, and re-assessing ventricular activity.

17. The method of claim 16, wherein generating the AT characteristic includes one or more of:
detecting an onset of an AT episode using the received physiologic information during the first time period;
detecting a termination of the AT episode using the received physiologic information during the second time period if the second AT indication indicates an absence of AT in the second time period; or
determining an AT episode duration from the detected onset to the detected offset of the AT episode.

18. The method of claim 15, wherein:
evaluating the VRS includes determining a count of unstable cardiac cycles within a specific time period or a specific number of cardiac cycles, the unstable cardiac cycle corresponding to a cycle length difference from a preceding cycle length exceeding a threshold; and
determining that the VRS satisfies an instability criterion if the count of unstable cardiac cycles exceeds a count threshold.

19. The method of claim 15, wherein:
evaluating the VRS includes initializing the VRS using a variability measure of cycle lengths of a plurality of cardiac cycles, and adaptively updating the VRS using a cycle length difference between a present cycle length and a preceding cycle length; and
determining that the VRS satisfies an instability criterion if the adaptively updated VRS exceeds a threshold value.

20. The method of claim 14, wherein the distinct time periods are consecutive time periods, and wherein triggering detection of respective AT indications involves using one or more of ventricular rate variability or ventricular signal morphology within the distinct time periods.

* * * * *